United States Patent [19]

Bondar et al.

[11] 4,107,089

[45] Aug. 15, 1978

[54] CATALYST FOR THE SYNTHESIS OF METHANOL AND METHOD FOR PREPARING SAME

[76] Inventors: Petr Grigorievich Bondar, prospekt Kosmonavtov, 15, kv. 12; Oleg Nikolaevich Goroshko, ulitsa Donetskaya, 54, kv. 24; Larisa Emmanuilovna Suschaya, prospekt Kosmonavtov, 15, kv. 52; Valentina Vasilievna Lavrova, ulitsa Avtomobilnaya, 7, kv. 49; Valentina Emmanuilovna Leleka, ulitsa Gagarina, 54-b, kv. 36; Eduard Grigorievich Ilko, ulitsa Parizhskoi Kommuny, 8, kv. 31, all of Severodonetsk Voroshilovgradskoi oblasti, U.S.S.R.

[21] Appl. No.: 777,333

[22] Filed: Mar. 14, 1977

[51] Int. Cl.$^2$ .................. B01J 21/04; B01J 21/10; B01J 23/06; B01J 23/26; B01J 23/28; B01J 23/30; B01J 23/72

[52] U.S. Cl. .................................. 252/465; 252/468; 260/449.5

[58] Field of Search .................. 252/465, 468; 260/449.5; 106/58, 59, 65, 66, 73.4

[56] References Cited

U.S. PATENT DOCUMENTS

| 3,256,208 | 6/1966 | Eguchi et al. ................ 252/468 |
| 3,326,956 | 6/1967 | Davies et al. .............. 252/468 X |

FOREIGN PATENT DOCUMENTS

| 1,123,657 | 2/1962 | Fed. Rep. of Germany ........... 252/468 |
| 1,159,035 | 7/1969 | United Kingdom .................. 260/449.5 |
| 1,205,156 | 9/1970 | United Kingdom .................. 260/449.5 |

*Primary Examiner*—W. J. Shine
*Attorney, Agent, or Firm*—Lackenbach, Lilling & Siegel

[57] ABSTRACT

A catalyst for the synthesis of methanol which contains an oxide of one or more metals of Group VI, chromium subgroup, of the periodic system, copper oxide, zinc oxide and an oxide of one or more hardly reducible metals of Group II–III of the periodic system.

The catalyst according to the present invention is prepared by precipitation, by means of sodium carbonate at a pH value within the range of from 5.5 to 7.5, of salts of copper, zinc and at least one hardly reducible metal of group II–III of the periodic system, whereafter the resulting precipitated mass is filtered-off, washed at pH=7–8, dried and added with soluble and readily thermally-decomposed compounds of one or more metals of Group VI, chromium subgroup, of the periodic system; then the resulting catalyst mass is dried and tabletted.

The catalyst according to the present invention features a higher efficiency, by 1.2–2 times superior to that of the prior art catalysts for the synthesis of methanol, and increased thermal stability during the operation. Furthermore, the catalyst according to the present invention demonstrates good operation characteristics when used in the synthesis of methanol under a pressure ranging from 50 to 80 atm.

15 Claims, No Drawings

CATALYST FOR THE SYNTHESIS OF METHANOL AND METHOD FOR PREPARING SAME

The present invention relates to the production of methanol and, more specifically, to a catalyst for the synthesis of methanol and to a method of preparing same.

The present invention is useful in the production of methanol; the latter is extensively used, for example, in the production of formaldehyde resins, synthetic fibres based on polyester resins, in the organic synthesis for methylation of intermediate products and as an additive for motor fuels.

The catalysts prepared according to the present invention may be employed in the synthesis of methanol from carbon monoxide and hydrogen under a pressure of from 30 to 60 atm, 80 to 150 atm, 200 to 300 atm at a temperature ranging from 200° to 280° C in the presence of carbon dioxide as well as under a pressure within the range of from 300 to 400 atm in the presence of carbon dioxide or without it at a temperature ranging between 260° to 400° C.

Furthermore, the catalyst according to the present invention can be employed for carbon monoxide conversion as well as in the processes of hydrogenation of organic compounds.

Known in the art is a catalyst (cf. U.S. Pat. No. 3,850,850) which has the following composition, percent by weight:

CuO: 24
ZnO: 38
$Al_2O_3$: 37,6
$Na_2O$: 0.1

This prior art catalyst is prepared in the following manner.

First aluminum and zinc are precipitated from solutions of their nitrates by means of sodium carbonate.

At the same time, basic copper and zinc carbonates are precipitated from solutions of their nitrates by means of soda.

Both suspensions are intermixed and maintained at a temperature of 60° C for 1 hour; the precipitate is filtered, washed with water, dried at 110° C, calcined at a temperature of 300° C and tabletted into tablets of 3.6×5.4 mm.

The presence of a large amount of $Al(OH)_3$ in the catalyst is known to hinder washing of alkali metals, e.g. sodium, from the catalyst due to high absorption ability of the hydroxide. Increased $Na_2O$ content in the catalyst composition results, as a rule, in reduced activity and selectivity of the catalyst.

The content of $Na_2O$ in the catalysts currently employed in industry under the conditions described in U.S. Pat. No. 3,850,850 should not exceed 0.05% by weight.

When using the catalyst prepared according to the procedure described in Example 1 of said U.S. patent and tested under a pressure of 350 atm at a temperature within the range of from 226° to 259° C from a circulating gas containing, percent by volume: carbon dioxide 0.6, carbon monoxide 4.0, hydrogen 66.8 and inert gases, i.e. a mixture of nitrogen, argon and methane 28.6 at a gas space velocity of 12,000 $hr^{-1}$ methanol output is not higher than 0.87 ml/ml of the catalyst per hour. This value is insufficient.

In the second Example of said U.S. patent a catalyst is described, incorporating, as calculated for metal, percent by weight:

copper: 59.8;
zinc: 25.6;
aluminum: 14.6.

When using a catalyst in a laboratory reactor under the pressure of 50 atm at a temperature of 250° C and the gas space velocity of 40,000 $hr^{-1}$ the methanol output is only 14.19% by volume of methanol in the reaction gas.

In West German Pat. No. 1,241,429 a catalyst for the synthesis of methanol is described, containing oxides (in terms of metal), percent by weight:

copper: 65 to 75
zinc + chromium: 25 to 35.

The catalyst is prepared by co-precipitation of said metals from solutions of their nitrates by means of soda; the precipitate is washed and dried, calcined and tabletted.

The catalyst features low activity and insufficient stability.

Thus, the methanol output is at most 0.62 ml of methanol per ml of the catalyst per hour.

Further known in the art is a catalyst (cf. U.S. Pat. No. 3,840,478) containing copper, zinc and chromium in the following atomic proportions (in terms of metal):

copper:zinc:chromium = (10–90):(5–70):(2–70).

The catalyst is prepared by mixing chromium anhydride with copper chromate in water. Basic copper carbonate and basic zinc carbonate are added to the above mixture in succession; the catalyst mass is dried at a temperature within the range of from 50° to 70° C, crushed, calcined at a temperature of 300° C for 30 hours in nitrogen flow and tabletted.

The catalyst was tested under a pressure of 40 atm at a temperature of 237° C and at a gas space velocity of 2,000 $hr^{-1}$ gave the methanol output of 14.2 vol.% of methanol in the reaction gas, which is clearly insufficient at that low space velocity.

According to British Pat. No. 1,159,035 a catalyst of the following composition (percent by weight, in terms of metal): copper over 20, preferably over 35; zinc less than 70; preferably from 15 to 50; and a third element selected from Groups II–IV of the periodic system such as aluminum, magnesium in an amount of from 4 to 20% by weight, is obtained by way of co-precipitation of salts of said metals in water by means of soda at a pH value of 6 to 9, preferably at a pH=7+0.5. The resulting precipitate is filtered, washed to remove alkali metal ions, dried, calcined and tabletted.

The methanol output when using said catalyst at a temperature of 240° C under a pressure of 50 atm is not more than 0.5 ml of methanol per ml of the catalyst per hour.

The stability of the copper-zinc-chromium catalyst, mentioned in the same British Patent and prepared by following the abovementioned procedure, is insufficient.

British Pat. No. 1,302,726 discloses a catalyst for the synthesis of methanol which synthesis is performed under a pressure of from 30 to 150 atm at a temperature within the range of from 200° to 350° C.

The catalyst contains (parts by weight in terms of metal): copper, 1 to 60, preferably 30 to 55; zinc, 1 to 65, preferably 1 to 35; manganese, 4 to 20, preferably 4 to 12; aluminum and chromium taken either in combination (7 to 20) or separately (3 to 6).

The catalyst is prepared by precipitation of copper, zinc, manganese, aluminum and/or chromium from solutions of their nitrates or acetates by means of sodium bicarbonate. The precipitation is conducted at a temperature within the range of from 85° to 100° C. The precipitate is filtered, washed to remove the precipitating agent, dried at a temperature within the range of 60° to 100° C and calcined at a temperature ranging between 250° and 270° C for a period of from 3 to 5 hours.

Graphite in an amount of 1 to 3% is added to the catalyst mass and the latter is tabletted.

According to British Pat. No. 1,302,726, the methanol output under a pressure of 50 atm at a temperature of 230° C is 1.43 ml/ml of the catalyst per hour, while under a pressure of 100 atm it is 2.6 ml of methanol per ml of the catalyst per hour.

It is an object of the present invention to overcome the above-mentioned disadvantages inherent in the prior art catalysts.

The main object of the present invention to provide a catalyst for the synthesis of methanol which would increase methanol output.

Another object of the present invention is to provide a catalyst for the synthesis of methanol which would possess an increased time stability.

Still another object of the present invention is to provide a method for preparing a catalyst for the synthesis of methanol which would enable the production of a catalyst featuring increased activity and time stability.

These objects are accomplished by a catalyst for the synthesis of methanol incorporating oxides of copper, zinc and an oxide of one or more difficult-to-reduce metals of Groups II–III of the periodic system and additionally contains, according to the present invention, an oxide of one or more metals of Groups VI, chromium subgroup, of the periodic system.

The catalyst according to the present invention features an increased efficiency (1.2–2 times as high as that of the prior art catalyst for the synthesis of methanol) and higher thermal stability during the operation;

To ensure higher reliability of the catalyst operation in the synthesis of methanol under pressures of about 50 atm, as the metal oxide of Group VI, chromium subgroup, of the periodic system, the catalyst according to the present invention, contains tungsten oxide taken in an amount ranging from 0.01 to 4.0% by weight.

To ensure higher efficiency and stability of the catalyst in the synthesis of methanol under a pressure of 80 atm and above, as the metal oxide of Group VI, chromium subgroup, of the periodic system, the catalyst according to the present invention, additionally contains chromium oxide in an amount ranging from 0.01 to 40.0% by weight; to enhance mechanical strength of the catalyst, it additionally contains 40 wt.% of zinc chromate.

It is advisable that the catalyst for the synthesis of methanol according to the present invention be prepared by a method wherein copper, zinc and at least one difficulty reducible metal of Groups II–III of the periodic system are precipitated by means of sodium carbonate from solutions of salts of said metals, whereafter the precipitated mass is filtered-off, washed, dried, calcined and tabletted. In accordance with the present invention, co-precipitation of said salts is conducted at a pH value of 5.5 to 7.5; the resulting mass is washed at a pH value of 7–8 at a temperature of 20° to 50° C and after calcination the mass is incorporated with soluble and readily-decomposable, during the heattreatment, compounds of one or more metals of Group VI, chromium subgroup, of the periodic system, whereafter the catalyst mass is dried and tabletted.

After drying and calcination of the catalyst mass, up to 4 wt % of a mixture can be introduced thereinto, consisting of zinc oxide and chromium anhydride, taken in an equimolecular ratio.

Owing to the method according to the present invention it has become possible to obtain a catalyst featuring an efficiency 1.2-2 times superior to that of the prior art catalysts employed for the synthesis of methanol, and higher thermal stability during the operation;

To prepare a catalyst featuring a high reliability of operation during the synthesis of methanol under the pressure of 50 atm, the catalyst mass, after its drying and calcination, is mixed with soluble and readily-decomposable, upon heat treatment, ammonium compounds of tungsten in an amount of from 0.01 to 4.0% by weight as calculated for the tungsten oxide employed.

For the same purpose, and also for increasing the mechanical strength of the catalyst after reduction, zinc chromate $ZnCrO_4$ is introduced into it in an amount of up to 4.0% by weight.

To prepare a catalyst featuring a higher efficiency and stability during the synthesis of methanol under a pressure of 80 atm and higher, the catalyst mass, after its drying, is mixed with chromium anhydride in an amount of from 0.01 to 40% by weight.

To prepare a catalyst featuring a higher thermal stability, chromium anhydride and magnesium hydroxide in an amount of 0.3 to 1.5% by weight are added simultaneously to the catalyst mass.

To prepare a catalyst featuring an increased activity under a pressure ranging between 300 to 400 atm and at a temperature within the range of 280° to 380° C, prior to introduction of chromium anhydride, zinc oxide in an amount of 15 to 60% by weight is added to the catalyst mass after drying.

These and other objects and advantages of the present invention will now become more fully apparent from the following detailed description of the catalyst for the synthesis of methanol, method for preparing same and Examples illustrating the method according to the present invention.

The catalyst for the synthesis of methanol according to the present invention contains oxides of copper, zinc and at least one oxide of hardly reducible elements selected from II-III Groups of the periodic system such as aluminum, magnesium or a mixture thereof. Furthermore, the catalyst according to the present invention incorporates oxides of one or more elements of Group VI, chromium subgroup, of the periodic system such as $CrO_3$, $MoO_3$, $WO_3$. The presence of said oxides in the catalyst according to the present invention either separately or in various combinations such as $CrO_3$ + $MoO_3$; $CrO_3$ + $WO_3$; $MoO_3$ + $WO_3$; $CrO$ + $MoO_3$ + $WO_3$ makes it possible to increase thermal stability of the catalyst.

It is known that copper-containing catalysts, prior to the their use, are subjected to reduction by various reducing agents such as hydrogen, carbon monoxide, methanol. In this case copper is fully converted into metallic state, It is also known that copper features high diffusive mobility at an elevated temperature in a reducing medium.

For this reason, in the course of the catalyst operation, copper becomes recrystallized, thus forming rather large agglomerates. This results in a lowered activity and reduced service life of the catalyst. Slowing down of copper recrystallization in conventional catalysts is effected, as is well known, by addition thereinto of hardly reducible oxides of metals pertaining to Groups II–III of the periodic system such as zinc oxide, magnesia, alumina.

We have found that incorporation of oxides of metals pertaining to Group VI, chromium subgroup, of the periodic system into copper-containing catalysts in addition to the above-mentioned compounds provides an additional opportunity to retain the copper-containing active phase of the catalyst in a highly dispersed state, thereby increasing thermal stability of the catalyst, i.e. retaining high efficiency of said catalyst for a long period of time.

The catalyst for the synthesis of methanol according to the present invention contains the components listed herein-below in specified combinations and amounts depending on the operating conditions during the synthesis of methanol, weight percent:

copper oxide: 8 to 60
zinc oxide: 20 to 60
alumina: 0.3 to 6.0
tungsten oxide: 0.01 to 4.0
and/or molybdenum oxide: 0.01 to 4.0
and/or magnesia: 0.3 to 1.5
and/or hexavalent chromium oxide: 0.01 to 40.

A catalyst prepared in accordance with the present invention and containing, percent by weight: copper oxide 52, zinc oxide 27, alumina 6, tungsten oxide 0.01 to 4.0, preferably 0.04 to 0.06, has been operated for 160 hours under the pressure of 50 atm at the temperature of 260° C without any noticeable decrease in the methanol output. Similar catalyst containing no tungsten has shown a twice-reduced output of methanol under the same process conditions.

A catalyst prepared in accordance with the present invention containing, in addition to copper, zinc and aluminum oxides, 0.05% by weight of tungsten trioxide, has been tested for thermal stability using the method of overheating. First the methanol output at temperatures of 220°, 240° and 260° C was determined, and then the catalyst was overheated at a temperature of 330° C for a period of 6 hours and the methanol output was again measured at the same temperatures. The coefficient of thermal stability determined as a ratio between the methanol outputs after the overheating and prior thereto in the presence of tungsten trioxide in the catalyst is 0.8 to 0.7, while that without tungsten trioxide is 0.4 to 0.5.

Incorporation of tungsten trioxide into copper-containing catalysts, according to the present invention, in an amount from 0.01 to 4% by weight decreases diffusive mobility of copper and sufficiently stabilizes the active surface of the catalyst.

The catalyst according to the present invention which contains, percent by weight:

copper oxide: 45
zinc oxide: 20
alumina: 5
chromium anhydride: 8–11 features an increased thermal stability; its coefficient of thermal stability is 1.0.

The catalyst according to the present invention does not decrease the methanol output upon overheating. The methanol output under the pressure of 50 atm and at the temperature of 260° C with space velocity of 10,000 hr$^{-1}$ is 2.25 ml/ml of the catalyst per hour. This increased thermal stability is due to the presence, in the catalyst, of zinc-chromium spinel ($ZnO.Cr_2O_3$) possessing high thermostabilizing properties.

We have found that the catalyst according to the present invention should contain not less than 0.01% by weight of chromium oxide, since only with this amount of the oxide, zinc-chromium spinel is formed in an amount sufficient for thermal stabilization of the catalyst. Increased content of chromium oxide (above 40% by weight) does not result in improved thermal stability.

The catalyst according to the present invention is prepared in the following manner.

A solution of, for example, copper, zinc and aluminum acetates or nitrates and a solution of sodium carbonate are mixed to perform co-precipitation at a temperature of 85° C and pH of 5.5 to 7.5, preferably at a pH of 6.0 to 6.5. The precipitating medium selected in accordance with the present invention ensures a more uniform precipitation of all three components, whereby the catalyst efficiency is increased.

On completion of the co-precipitation, the suspension, pH is brought to 7.0–7.5. The resulting precipitate is subjected to repeated washing, for example by way of decantation, and then filtered on a vacuum-filter or a filter-press and washed with water. In this case it is necessary that the pH of the washing be not less than 7.0 to 8.0 and temperature not be above 50° C, since under these conditions a better separation of harmful impurities such as sodium nitrate is obtained. The resulting precipitate of basic carbonates of copper, zinc and aluminum hydroxide is dried at a temperature of 120° C for 10 hours to a humidity content of 2–4% and then calcined in the air at a temperature of 300° C for 6 hours to remove carbon dioxide and moisture from the catalyst mass. The calcination results in the formation of a highly developed surface of the active phase of the catalyst which but slightly changes during further reduction.

In accordance with the present invention, after calcination, the precipitate is incorporated with soluble readily decomposed, upon heat treatment, compounds of one or more metals of Group VI, chromium subgroup, of the periodic system such as tungstenates, molybdates, ammonium chromates, chromium anhydride. These compounds can be incorporated into the catalyst according to the present invention either separately or in combination.

Said compounds are water-soluble, therefore the catalyst mass can be uniformly impregnated with their solutions. Furthermore, they are readily decomposed at a temperature within the range of 200° to 250° C. Therewith, the stabilizing additive in the form of a corresponding oxide or a mixture of oxides remains at the surface.

In accordance with the present invention, the effect of the catalyst stabilization is obtained by incorporating, into the catalyst composition, tungsten trioxide in an amount of from 0.01 to 4.0% by weight.

After incorporation of the ammonium tungstenate into the catalyst mass, the latter is subjected to repeated drying at a temperature of 120° C for 10 hours, whereafter it is mixed with 2% of graphite and tabletted.

In a similar manner such stabilizing additives are $MoO_3$, $CrO_3$ as well as mixtures of $CrO_3 + MoO_3$; $CrO_3 + WO_3$; $MoO_3 + WO_3$; $CrO_3 + MoO_3 + WO_3$ are introduced into the catalyst.

The catalyst prepared according to the present invention features a higher methanol output as compared to the catalysts prepared by a prior art methods. Thus, at the temperature of 240° C, when using the catalyst of the present invention, the methanol output is 1.7 ml/ml of the catalyst per hour, whereas a sample of the catalyst prepared by the prior art method gives only 0.75 ml/ml of the catalyst per hour.

The method for preparing a chromium-containing catalyst according to the present invention consists in drying and treating the precipitate of basic copper, zinc and aluminium hydroxide carbonates with chromium anhydride in an amount of 0.01 to 40% by weight in the presence of water. Owing to the ability of chromic acid to react with basic copper and zinc carbonates at an approximately equal rate, a uniform distribution of copper chromate in zinc chromate occurs.

In the process of the catalyst reduction, copper chromate, while decomposing, liberates free copper which is distributed and retained in a highly dispersed state owing to the presence of a stabilizing phase, i.e. zinc-chromium spinel.

The precipitate treated with chromium anhydride in accordance with the present invention is further subjected to calcination to decompose the carbonates and then mixed with graphite and tabletted.

In order to additionaly increase thermal stability of the catalyst according to the present invention, the catalyst may be incorporated, in addition to chromium anhydride, with magnesium hydroxide in an amount of from 0.3 to 1.5% by weight as found experimentally.

Thus, a catalyst containing 48% by weight of copper oxide, 25.5% by weight of zinc oxide, 4.5% by weight of alumina, 0.7% by weight of magnesia, 15% by weight of chromium oxide (calcination losses are 6.3%) makes it possible, under a pressure of 100 atm, space velocity of 10,000 $hr^{-1}$; $H_2:CO = 2.0:1$; $CO_2$ content of 8 to 10% and at a temperature of 280° C, to reach a methanol output of 4 ml/ml of the catalyst per hour, which corresponds to the methanol content in the reaction gas of 24% by weight. The coefficient of thermal stability of the catalyst is 1.0.

A catalyst having the composition: 35% by weight of copper oxide, 15% by weight of zinc oxide, alumina 5.5% by weight, 0.5% by weight of magnesia, 35% by weight of chromium oxide (calcination losses are 9%), prepared by the method according to the present invention, makes it possible to reach, under a pressure of 250 atm, space velocity of 40,000 $hr^{-1}$, $H_2:CO = 2:1$; $CO_2$ content of 8–10%, at a temperature of 300° C, a methanol output of 12.0 ml/ml of the catalyst per hour, the content of methanol in the reaction gas is 19.0% by volume.

The method for preparing a catalyst for the synthesis of methanol according to the present invention involves intermixing the mass containing basic copper, zinc and ammonium hydroxide carbonates (prepared by co-precipitation) with zinc oxide and chromium anhydride in dry state to a uniform mass, followed by treatment with water in an amount ensuring the ratio of the liquid phase to the solid one (L:S) of up to 0.6 for a period of 1–2 hours. The catalyst is then dried and tabletted. Zinc oxide incorporated in an amount of 15 to 60% by weight ensures the formation of zinc-chromium spinel in a sufficient concentration, thus ensuring high thermal stability of the catalyst. The catalyst prepared by the method according to the present invention features increased methanol output.

Thus, a catalyst having the following composition, percent by weight: copper oxide 8, zinc oxide 55, chromium oxide 28, alumina 0.3–0.5 under a pressure of 250 atm, gas space velocity of 40,000 $hr^{-1}$, $H_2:CO = 2:1$ at a temperature of 340° C, makes it possible to achieve a methanol output of 10.4 ml/ml of the catalyst per hour or 16.6% by volume methanol content in the reaction gas. Using a conventional zinc-chromium catalyst the maximal rate of methanol formation is 5.9 ml/ml of a catalyst per hour is achieved at the temperature of 380° C.

The specific Examples given hereinbelow illustrate certain possible embodiments of the present invention without, however, limiting its spirit and scope.

EXAMPLE 1

A solution of 27.5 g of aluminum nitrate in 230 ml of water is poured into a solution of 435 g of $Cu(NO_3)_2 \times 3H_2O$ and 269 g of $Zn(NO_3)_2 \times 6H_2O$ in 1,300 ml of water. The mixture of said salts is gradually mixed with 52–56% solution of nitric acid. The addition is effected to a content of free acid in the solution of 3–4%. The resulting solution is heated to a temperature of 80° to 85° C and at this temperature co-precipitation by means of sodium bicarbonate is performed at a rate of combining the solutions of 500 to 600 l/hr at pH of 6±0.3; at the end of co-precipitation pH of the solution is brought to 7.0.

The resulting precipitate is subjected to washing by means of a repeated decantation at a temperature of 40° to 45° C and pH of 7 to 7.5. (To adjust pH of the suspension an ammonia solution is added, when required, and washing is continued). After washing a precipitate is filtered, dried at a temperature of 120° C and calcined at a temperature within the range of 250° to 300° C. The resulting mass is then impregnated with a solution of the stabilizing additive salt to have 0.03 to 0.06% by weight of tungsten trioxide in the final catalyst. The catalyst is dried and tabletted with 2.% of graphite. The final catalyst is then tested at the temperature of 260° C under the pressure of 50 atm, gas space velocity of 10,000 $hr^{-1}$, $H_2:CO$ ratio equal to 2.2:1 and CO content of 8 to 10%. The tests have revealed that the catalyst efficiency remains practically unchanged after 160 hours of operation and constitutes 1.0 kg of a 100% methnol per 1 liter of the catalyst per hour.

A sample of the catalyst prepared by the prior art method when operated under similar conditions for 160 hours has lowered its activity by 50% of the initial value.

EXAMPLE 2

52 kg of copper powder, 31.7 kg of zinc oxide and 53.7 kg of aluminum nitrate nonanhydrate are mixed with 500 l of desalted water. The mixture of said salts is gradually mixed with 52–56% of nitric acid. The addition continues until to a free acid content in the solution of 3–4%, whereafter an additional 1,000 l of desalted water are poured into the reaction mass. Co-precipitation and the precipitate washing are performed by the procedure described in Example 1 herein-above.

After washing the precipitate is filtered, and dried at a temperature of 120° C for 24 hours. The dry mass is calcined for 6 hours at a temperature of 300° C, mixed with 2% of graphite and tabletted into tablets of the 5×5 mm; the resulting tablets are crushed and a fraction of a 2–3 mm particle size is selected. This fraction is tested for efficiency in a synthesis of methanol under the pressure of 50 atm, gas space velocity of 10,000 hr$^{-1}$, H$_2$:CO ratio of 2.2:1 and CO$_2$ content of 3 to 10 vol.% with the catalyst intermixing with a 5-fold volume of copper. The test results are given in Table 1 hereinbelow.

Table 1

| Catalyst | Amount of the resulting 100% methanol, g/ml of the catalyst per hour at | | |
|---|---|---|---|
| | 220° C | 240° C | 260° C |
| Sample prepared by a conventional method | 0.32 | 0.60 | 0.80 |
| Sample prepared by the method according to the present invention | 0.75 | 1.38 | 1.30 |

EXAMPLE 3

Prior to co-precipitation, to the starting solution of salts for the preparation of the catalyst according to the procedure of Example 1 a solution of the stabilizing tungsten salt (NH$_4$)$_4$W$_5$O$_{17}$×2.5H$_2$O is added in an amount to have 0.5% by weight of tungsten trioxide in the final catalyst. Preparation of the catalyst and its tests are performed in a manner similar to that described in Example 1 hereinbefore, except the temperature conditions. The catalyst is first tested at the temperatures of 220° and 240° C, then heated at the temperature of 330° C for 6 hours, whereafter it is again tested at 220° and 240° C.

The data illustrating the catalyst efficiency at 220° C and 240° C, kg of the resulting 100% methanol per liter of the catalyst per hour are shown in Table 2 hereinbelow.

Table 2

| Catalyst | Temperature, ° C | Catalyst efficiency, kg of 100% methanol/l of the catalyst per hour | | Catalyst stability (ratio of the final efficiency to the initial one) |
|---|---|---|---|---|
| | | initial | final | |
| 1. Catalyst of Example 2 | 220 | 0.75 | 0.4 | 0.53 |
| | 240 | 1.38 | 0.75 | 0.54 |
| 2. Catalyst according to the invention containing 0.5% of tungsten oxide added at the co-precipitation stage | 220 | 0.85 | 0.67 | 0.80 |
| | 240 | 1.53 | 1.07 | 0.70 |

EXAMPLE 4

40 kg of a dried non-calcined mass prepared by co-precipitation of salts of copper, zinc and aluminum by the procedure described in Example 1 hereinbefore are treated in a mixer with a solution containing 3.2 kg of chromium anhydride and 20 l of water. The catalyst mass is dried at a temperature of 110° C for 4 hours, calcined at a temperature of 300° C for 6 hours, tabletted into tablets of the 5×5 mm and crushed to fractions of a 2-3 mm particle size. The catalyst is tested under the conditions described in Example 1 hereinbefore at a temperature within the range of from 220° to 260° C. The test results are shown in Table 3 hereinbelow.

Table 3

| Catalyst | Temperature, ° C | Amount of the resulting methanol (100%) g/ml of the catalyst per hour | | Catalyst stability (ratio of the final efficiency to the initial one) |
|---|---|---|---|---|
| | | before overheating | after overheating | |
| The catalyst including 8% of the stabilizing additive, i.e. chromium oxide | 260 | 1.81 | 1.76 | 0.97 |
| | 240 | 1.43 | 1.43 | 1.00 |
| | 220 | 0.76 | 0.66 | 0.87 |

EXAMPLE 5

40 kg of a dried non-calcined mass prepared by co-precipitation of salts of copper, zinc and aluminum by the procedure described in the foregoing Example 1 are treated in a mixer with a solution containing 4.4 kg of chromium anhydride and 18 l of water. The resulting catalyst mass is further treated and the final catalyst is tested in a manner similar to that described in Example 4 hereinabove. The data illustrating the catalyst properties revealed in the tests are given in Table 4 hereinbelow.

Table 4

| Catalyst | Temperature, ° C | Amount of the resulting 100% methanol, g/ml of the catalyst per hour | | Catalyst stability (ratio of the final efficiency to the initial one) |
|---|---|---|---|---|
| | | before overheating | after overheating | |
| Catalyst involving 11% of the stabilizing additive, i.e. chromium oxide | 260 | 1.15 | 1.61 | 1.39 |
| | 240 | 1.05 | 1.05 | 1.00 |
| | 220 | 0.67 | 0.65 | 0.97 |

EXAMPLE 6

1.5 l of catalyst containing 53% by weight of chromium oxide, 26.0% by weight of zinc oxide, 5.5% by weight of alumina, 0.05% by weight of tungsten trioxide, 6.0% of carbonates as calculated for CO$_2$, and water — the balance, prepared in accordance with the present invention is employed in the synthesis of methanol at a temperature within the range of 200° to 250° C under the pressure of 50 atm, gas space velocity of 11,980 hr$^{-1}$, calculating gas composition, vol;%:

| | | | |
|---|---|---|---|
| carbon dioxide | 9.15 | carbon monoxide | 15.60 |
| hydrogen | 47.35 | methane | 14.40 |
| nitrogen | 12.80 | ethylene | 0.02 | at the ratio of H$_2$:CO = 3.04 and the ratio (H$_2$ − CO$_2$)/(CO + CO$_2$) = 1.55.

Therewith, 14.9 ton of 100% methanol are obtained per m$^3$ of the catalyst per day; water content in the crude methanol is 8.1%. Organic portion of the crude methanol contains, per cent by weight:

methanol: 99.341
dimethyl ether: 0.1493
n-propanol: 0.1800
isobutanol: 0.0637;

impurities such as aldehydes, ketones and the like being the balance.

EXAMPLE 7

A catalyst prepared under conditions similar to those described in Example 1 hereinbefore is charged, in the amount of 1.7 m³, in a column for the synthesis of methanol and the process is conducted under the following conditions; pressure 50 atm; space velocity 9,054 hr⁻¹; temperature 230° to 280° C; circulating gas composition, vol.%; carbon dioxide 3.92; carbon monoxide 24.39; hydrogen 48.61; methane + nitrogen 20.30; $H_2$:CO ratio is equal to 2.2:1.

Therewith, 9.07 tons of methanol from 1 m³ of the catalyst per day are formed at the following composition of the organic portion of methanol:
methanol: 99.193
dimethyl ether: 0.219
n-propanol: 0.1520
isobutanol: 0.0509;
impurities such as aldehydes, ketones and the like being the balance.

EXAMPLE 8

40 kg of a dried catalyst mass prepared by co-precipitation according to the procedure described in Example 1 hereinbefore are gradually intermixed with a solution containing 5.6 kg of chromium anhydride, 0.37 kg of magnesium hydroxide and 15 l of water. The resulting mass is dried at the temperature of 110° C for 4 hours, calcined at a temperature of 340° C for 6 hours and tabletted into tablets with a size of 5×5 mm. The catalyst is then crushed and the fraction of 2–3 mm particle size is selected and tested at a temperature within a range of 240° to 280° C, under the pressure of 100 atm, gas space velocity of 10,000 hr⁻¹. The initial gas contains 5% of $CO_2$ and has the ratio $H_2$:CO = 2:1.

The catalyst efficiency prior to overheating at a temperature of 350° C for 6 hours and thereafter expressed as g of 100% methanol per 1 ml of the catalyst per hour is shown in Table 5 hereinbelow.

Table 5

| Testing temperature, °C | Amount of the resulting 100% methanol, g/ml of the catalyst per hour | | Catalyst stability (ratio of the final efficiency to the initial one) |
|---|---|---|---|
| | before overheating | after overheating | |
| 280 | 3.1 | 3.1 | 1.0 |
| 260 | 2.4 | 2.4 | 1.0 |
| 240 | 1.6 | 1.7 | 1.06 |

EXAMPLE 9

A catalyst having the following composition, percent by weight: copper oxide 42.4; zinc oxide 22.6; chromium oxide 14.1; alumina 4.5; magnesia 0.7; carbon dioxide 6.0, water being the balance, prepared by the procedure described in the foregoing Example 5 is charged, in the amount of 0.75 m³, into a column for the synthesis of methanol and the process is conducted at a temperature within the range of 235° to 285° C, under the pressure of 100 atm, gas space velocity of 17,000 hr⁻¹; the circulating gas has the following composition, percent by volume; carbon dioxide, 5; carbon monoxide 9.2; hydrogen 45.0; methane + nitrogen 40.8; the ratio of $H_2$ to CO is more than 2:1. One m³ of the catalyst gives 14.5 ton of methanol per day. Water content in the crude methanol is 7.9%. Organic portion of the crude methanol contains, percent by weight: methanol 99.3; dimethyl ether 0.4; methylformate 0.15; impurities such as aldehydes, ketones and the like being the balance.

EXAMPLE 10

31.5 kg of a dried mass prepared by co-precipitation of copper, zinc and aluminum salts performed by the procedure described in Example 1 hereinbefore, are charged into a mixer. The mass is then intermixed, with a solution containing 8.5 kg of chromium anhydride, 0.275 kg of magnesium hydroxide and 11.5 l of water.

The resulting catalyst mass is dried at a temperature of 110° C, calcined at a temperature of 340° C for 6 hours and tabletted into 5×5 mm tablets. The catalyst is then crushed, the fraction of 2–3 mm particle size is selected and tested at a temperature within the range of from 260° to 320° C, under a pressure of 250 atm, gas space velocity of 40,000 hr⁻¹, ratio of $H_2$ to CO = 2.2; $CO_2$ content of 8 to 10 vol.%. To determine the catalyst stability, it is overheated at a temperature of 350° C for 6 hours. The data illustrating the catalyst efficiency are given in Table 6 hereinbelow.

Table 6

| Testing temperature, °C | Amount of the resulting 100% methanol, kg/l of the catalyst per hour | | Catalyst stability (ratio of the final efficiency to the initial one) |
|---|---|---|---|
| | before overheating | after overheating | |
| 260 | 5.0 | 4.9 | 1.0 |
| 280 | 4.8 | 5.5 | 1.1 |
| 300 | 9.5 | 8.0 | 0.84 |
| 320 | 12.0 | 9.0 | 0.75 |

EXAMPLE 11

The catalyst prepared by the procedure described in Example 10 hereinabove is tested in tablets of 5×5 mm size at a temperature of 260° C, under a pressure of 300 atm, gas space velocity of 34,000 to 36,000 hr⁻¹, ratio of $H_2$ to CO of 4 to 6, $CO_2$ content in the gas of 4 to 6% by volume; inert products ($CH_4 + N_2$) content of 25% by volume. Therewith, the resulting 100% methanol amount is 49 t per m³ of the catalyst per day.

EXAMPLE 12

53.5 g of a non-calcined catalyst mass prepared by the procedure described in the foregoing Example 1 are mixed with 80.3 g of finely ground chromium anhydride and 100 g of zinc oxide. 154 ml of distilled water are added to the mixture and stirred until a mass of uniform consistency is obtained. The resulting paste-like mass is dried, crushed, the fraction with a particle size of 0.5–0.25 mm is selected, reduced by a conventional method and tabletted. The tablets are crushed, the fraction of 2–3 mm particle size is selected and employed in the synthesis of methanol under a pressure of 250 atm, at a temperature within the range of 300° to 360° C, space velocity of 40,000 hr⁻¹ and ratio of $H_2$ to CO more than 2:1. The data illustrating the catalyst efficiency expressed as ml of the crude methanol per ml of the catalyst per hour are given in Table 7 hereinbelow.

Table 7

| Catalyst | Amount of the resulting 100% methanol, ml/ml of the catalyst per day at temperatures: | | | | |
|---|---|---|---|---|---|
| | 300° C | 320° C | 340° C | 360° C | 380° C |
| Catalyst prepared according to the present invention | 3.9 | 6.4 | 10.4 | 7.7 | — |
| Catalyst prepared by a conventional method | 1.6 | 2.6 | 4.2 | 5.7 | 5.9 |

EXAMPLE 13

To 30 kg of a dried catalyst mass prepared by the procedure described in the foregoing Example 1 a mixture is added consisting of 60 kg of finely ground chromium anhydride and 77 kg of zinc oxide. 60 l of distilled water are then poured into the mixture, intermixed to give a uniform granulated mass which is then dried at a temperature of 40° C. The dried mass is tabletted into tablets of 9×9 mm which are employed in a synthesis of methanol under the pressure of 250 atm, at a temperature ranging between 260° and 380° at a gas space velocity of 40,000 hr$^{-1}$, H$_2$/CO ratio of 2.2:1. Characteristics of the catalyst according to the present invention and those of the catalyst prepared by a conventional method given for the comparison purposes are shown in Table 8 hereinbelow.

Table 8

| Catalyst | Amount of the resulting crude methanol, ml/ml of the catalyst per hour, at temperatures: | | | | | |
|---|---|---|---|---|---|---|
| | 260° C | 280° C | 300° C | 320° C | 350° C | 380° C |
| Catalyst prepared by the method according to the present invention | 5.4 | 5.6 | 6.7 | 7.0 | 5.0 | 5.0 |
| Catalyst prepared by conventional method | 1.2 | 2.0 | 2.9 | 4.0 | 5.4 | 5.0 |

EXAMPLE 14

100 g of a catalyst mass prepared as described in Example 1 are mixed with 1 g of zinc oxide, and then a solution is added to the mixture, containing, in addition to ammonium tungstenate 1 g of chromic anhydride. Zinc oxide and chromic anhydride give zinc chromate. The resulting homogeneous mass is tabletted. The catalyst thus prepared possesses good thermal stability, and the strength of the tablets after reduction two-fold as compared to the catalyst not treated with zinc chromate.

What is claimed is:

1. A catalyst composition for the synthesis of methanol consisting essentially of: copper oxide, zinc oxide and tungsten oxide; and at least one oxide of a difficultly reducible metal selected from the group consisting of aluminum and magnesium.

2. The catalyst composition of claim 1, wherein copper oxide exists in an amount varying from 8 to 60 weight %.

3. The catalyst composition of claim 1, wherein zinc oxide exists in an amount varying from 20 to 60 weight %.

4. The catalyst composition of claim 1, wherein aluminum oxide exists in an amount varying from 0.3 to 6 weight %.

5. The catalyst composition of claim 1, wherein magnesium oxide exists in an amount varying from 0.3 to 1.5 weight %.

6. The catalyst composition of claim 1, further including molybdenum oxide in an amount varying from 0.01 to 4.0 weight %.

7. The catalyst composition of claim 1, further including chromium oxide in an amount varying from 0.01 to 40 weight %.

8. The catalyst composition of claim 1, wherein tungsten oxide varies from 0.1 to 4.0 weight %.

9. The catalyst composition of claim 1, further including zinc chromate in amounts of up to 4.0 weight %.

10. A method for preparing a catalyst for the synthesis of methanol, which comprises:
   precipitating copper, zinc and at least one oxide of a difficultly reducible metal selected from the group consisting of aluminum and magnesium, by means of sodium carbonate, from solutions of their respective salts at a pH varying from 5.5 to 7.5;
   washing the precipitate at a pH varying from 7 to 8 and temperature varying from 20° to 50° C;
   drying and calcining said precipitate;
   incorporating into the precipitate an oxide of at least one Group VIB metal selected from the group consisting of chromium, molybdenum and tungsten.

11. The method of claim 10, wherein the catalyst composition is tabletted prior to its use in synthesis.

12. The method of claim 10, wherein said Group VIB metal oxide is selected from tungsten and molybdenum in amounts varying from 0.1 to 4 weight %.

13. The method of claim 10, wherein said Group VIB metal oxide is chrominum in amounts varying from 0.01 to 40 weight %.

14. The method of claim 10, wherein said Group VIB metal oxide is tungsten, furnished as a readily thermally decomposable ammonium compound of tungsten in amounts varying from 0.01 to 4 weight %, calculated on the basis of tungsten oxide.

15. The method of claim 10, wherein after drying and calcining, a mixture of up to 4 weight % of zinc oxide and chromium anhydride, in an equimolar ratio, is incorporated into the precipitate.

* * * * *